United States Patent
Hasegawa et al.

(10) Patent No.: US 10,012,628 B2
(45) Date of Patent: Jul. 3, 2018

(54) MULTIFUNCTIONAL PARTICLE ANALYSIS DEVICE AND METHOD OF CALIBRATING THE SAME

(71) Applicant: Fuji Electric Co., Ltd., Kanagawa (JP)

(72) Inventors: Yoshiki Hasegawa, Tokyo (JP); Kazuhiro Koizumi, Kanagawa (JP); Takamasa Asano, Tokyo (JP); Naoki Takeda, Kanagawa (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 4 days.

(21) Appl. No.: 15/067,772

(22) Filed: Mar. 11, 2016

(65) Prior Publication Data

US 2016/0377539 A1    Dec. 29, 2016

(30) Foreign Application Priority Data

Jun. 23, 2015    (JP) .................... 2015-125994

(51) Int. Cl.
*G01N 15/02* (2006.01)
*G01N 33/00* (2006.01)
(Continued)

(52) U.S. Cl.
CPC ..... *G01N 33/0004* (2013.01); *G01N 15/0205* (2013.01); *G01N 15/1012* (2013.01);
(Continued)

(58) Field of Classification Search
CPC .......... G01N 33/0006; G01N 15/0205; G01N 15/1012; G01N 15/1459; G01N 15/02;
(Continued)

(56) References Cited

U.S. PATENT DOCUMENTS 4,383,171 A * 5/1983 Sinha ............... G01N 30/72
                                                  250/282
4,458,150 A * 7/1984 Matsuda ............ H01J 49/26
                                                  250/298
(Continued)

FOREIGN PATENT DOCUMENTS

JP    2012-189483 A    10/2012
WO    2011/114587 A1    9/2011

*Primary Examiner* — Kara E Geisel
*Assistant Examiner* — Maurice Smith
(74) *Attorney, Agent, or Firm* — Chen Yoshimura LLP (57) ABSTRACT

A multifunctional particle analysis device includes a particle measuring device and a particle composition analysis device. Calibration particles for which at least the number, size, and composition thereof are known are input to the particle measuring device and the particle composition analysis device and analyzed. The sensitivity of the particle measuring device is calibrated in accordance with the number and size of the calibration particles as measured by the particle measuring device, and the sensitivity of the particle composition analysis device is calibrated in accordance with the mass composition of the calibration particles as measured by the particle composition analysis device. Moreover, the irradiation axis of particles that enter the particle composition analysis device relative to a capturing unit is calibrated in accordance with a state in which the calibration particles are captured on the capturing unit of the particle composition analysis device.

20 Claims, 8 Drawing Sheets

(51) Int. Cl.
*G01N 15/10* (2006.01)
*G01N 15/00* (2006.01)
*G01N 15/14* (2006.01)

(52) U.S. Cl.
CPC . G01N 15/1459 (2013.01); *G01N 2015/0046* (2013.01); *G01N 2015/1486* (2013.01); *G01N 2015/1493* (2013.01)

(58) Field of Classification Search
CPC ... G01N 2015/1486; G01N 2015/1493; G01N 30/72; G01N 2001/2223; H01J 49/26; H01J 49/164
See application file for complete search history.

(56) References Cited

U.S. PATENT DOCUMENTS

| | | | |
|---|---|---|---|
| 5,285,064 A * | 2/1994 | Willoughby | H01J 49/049 250/283 |
| 2001/0048366 A1 * | 12/2001 | Ikeda | G01N 15/02 340/627 |
| 2003/0114986 A1 * | 6/2003 | Padmanabhan | G06F 19/3493 702/1 |
| 2005/0105077 A1 * | 5/2005 | Padmanabhan | G01N 15/1484 356/39 |
| 2007/0165225 A1 * | 7/2007 | Trainer | G01N 15/0205 356/335 |
| 2009/0128810 A1 * | 5/2009 | Bates | G01N 15/1012 356/336 |
| 2012/0001067 A1 * | 1/2012 | Orii | G01N 15/0266 250/288 |
| 2013/0011930 A1 | 1/2013 | Takegawa et al. | |
| 2014/0247450 A1 * | 9/2014 | Han | G01N 15/0211 356/338 |

* cited by examiner

MULTIFUNCTIONAL PARTICLE ANALYSIS DEVICE AND METHOD OF CALIBRATING THE SAME

BACKGROUND OF THE INVENTION

Technical Field

The present invention relates to a multifunctional particle analysis device suitable for performing a variety of analyses on particles suspended in a gas such as air (that is, an aerosol) and to a method of calibrating the same.

Background Art

In recent years, there has been increasing concern over the health effects of fine particles (of size PM2.5 or the like) in the atmosphere, and research and development of devices for analyzing the mass concentration and composition of such fine particles has proceeded on various fronts. Patent Document 1, for example, discloses a particle measuring device in which an aerosol sample is enveloped with sheath air to form that sample into a beam shape, the resulting flow path is irradiated with laser light, and the scattered light produced when the laser light hits the particles is received using a light-receiving unit. This type of device makes it possible to calculate the number and size (or size distribution) of the particles according to electrical signals output in accordance with the received light. Moreover, Patent Document 2, for example, discloses a fine particle composition analysis device in which an aerosol sample is formed into a beam shape using an aerodynamic lens while removing the gas-phase components, and after the particles are captured by irradiating a capturing unit with the particle beam, the particles captured by the capturing unit are irradiated with energy beams to make the particles vaporize, sublimate, or react so as to produce desorption components, and the resulting desorption components are then analyzed. In this type of device, the particles in the aerosol sample are captured very selectively in a relatively small region, and the desorption components produced by irradiating those particles with energy beams are then analyzed. This makes it possible to analyze the composition and mass of the particles efficiently and with high sensitivity. Even more recently, there has been an increased amount of active research and studies in which not only is the number, size, and composition by mass of the particles measured, the resulting data is used to identify the source of the particles. Therefore, there are increasingly high requirements on multifunctional particle analysis devices suitable for performing a variety of analyses on such particles to be measured.

RELATED ART DOCUMENTS

Patent Documents

Patent Document 1: Japanese Patent Application Laid-Open Publication No. 2012-189483
Patent Document 2: WO 2011/114587

SUMMARY OF THE INVENTION

Analysis devices typically need to have a prescribed sensitivity in order to be able to correlate the strength of signals output when the substance to be measured is supplied to the device with a positive absolute value measurement of that substance. However, it is normal for the sensitivity of an analysis device to change from the initial state due to usage conditions and the length of time for which the device is used, and therefore the user has to periodically calibrate the device. In devices such as the particle measuring device disclosed in Patent Document 1, for example, the sensitivity of the device must be calibrated so that when reference particles of a known number and size are supplied to the device, those particle characteristics can be detected with a prescribed sensitivity. Furthermore, in devices such as the fine particle composition analysis device disclosed in Patent Document 2, the sensitivity of the device must be calibrated so that when reference particles of a known composition are supplied to the device, that composition can be detected with a prescribed sensitivity. Moreover, if the position at which particles that enter the device are captured by the capturing unit gets shifted away from the energy beam irradiation region, the composition and mass of the particles can no longer be analyzed correctly. Therefore, the capturing position must also be calibrated. Performing these types of calibrations one by one takes an extremely large amount of time and effort.

In view of these problems, the present invention aims to provide a multifunctional particle analysis device and a method of calibrating the same in which a plurality of devices for performing a variety of analyses on particles to be measured are integrated into the multifunctional particle analysis device and in which the periodic calibration operations required to maintain and improve the long-term reliability of the device can be performed easily and accurately. Accordingly, the present invention is directed to a scheme that substantially obviates one or more of the problems due to limitations and disadvantages of the related art.

Additional or separate features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve these and other advantages and in accordance with the purpose of the present invention, as embodied and broadly described, in one aspect, the present disclosure provides a method of calibrating a multifunctional particle analysis device including a particle measuring device that irradiates particles in an aerosol to be measured with laser light and measures a number and a size of the particles in accordance with scattered light produced when the laser light hits the particles, and a particle composition analysis device in which the particles in the aerosol to be measured are captured using a capturing unit and then irradiated with an energy beam to make the captured particles vaporize, sublimate, or react so as to produce desorption components, the desorption components being analyzed in order to analyze a composition and a mass composition of the particles, the method of calibrating including: inputting calibration particles for which at least a number, size, and composition thereof are known into the particle measuring device and the particle composition analysis device and then analyzing the calibration particles; calibrating a sensitivity of the particle measuring device in accordance with the number and the size of the calibration particles as measured by the particle measuring device; and calibrating a sensitivity of the particle composition analysis device in accordance with a mass composition of the calibration particles as measured by the particle composition analysis device.

The method of calibrating the multifunctional particle analysis device in one aspect of the present invention makes it possible to calibrate the sensitivity of the particle measuring device and the sensitivity of the particle composition analysis device at the same time and using the same calibration particles, thereby making it possible to reduce the effort required to calibrate the device in comparison with using separate calibration procedures.

In one aspect, the present disclosure provides a method of calibrating a multifunctional particle analysis device including a particle measuring device that irradiates particles in an aerosol to be measured with laser light and measures a number and a size of the particles in accordance with scattered light produced when the laser light hits the particles, and a particle composition analysis device in which the particles in the aerosol to be measured are captured using a capturing unit and then irradiated with an energy beam to make the captured particles vaporize, sublimate, or react so as to produce desorption components, the desorption components being analyzed in order to analyze a composition and a mass composition of the particles, the method of calibrating including: inputting calibration particles for which at least a number, size, and composition thereof are known into the particle measuring device and the particle composition analysis device and then analyzing the calibration particles; calibrating a sensitivity of the particle measuring device in accordance with the number and the size of the calibration particles as measured by the particle measuring device; and calibrating an irradiation axis of particles that enter the particle composition analysis device relative to the capturing unit in accordance with a state in which the calibration particles are captured on the capturing unit.

The method of calibrating the multifunctional particle analysis device in one aspect of the present invention makes it possible to calibrate the sensitivity of the particle measuring device and the irradiation axis of particles that enter the particle composition analysis device relative to the capturing unit at the same time and using the same calibration particles, thereby making it possible to reduce the effort required to calibrate the device in comparison with using separate calibration procedures.

In the method of calibrating the multifunctional particle analysis device in one aspect of the present invention, it is preferable that the sensitivity of the particle measuring device be calibrated according to the number and the size of the calibration particles as measured by the particle measuring device, that the sensitivity of the particle composition analysis device be calibrated according to the mass composition of the calibration particles as measured by the particle composition analysis device, and that the irradiation axis of particles that enter the particle composition analysis device relative to the capturing unit be calibrated in accordance with a state in which the calibration particles are captured on the capturing unit. This makes it possible to calibrate the sensitivity of the particle measuring device, calibrate the sensitivity of the particle composition analysis device, and calibrate the irradiation axis of particles that enter the particle composition analysis device relative to the capturing unit all at the same time and using the same calibration particles, thereby making it possible to reduce the effort associated with calibrating the device in comparison with using separate calibration procedures.

In the method of calibrating the multifunctional particle analysis device in one aspect of the present invention, it is preferable that the calibration particles be visibly marked. This makes it possible to easily verify the state in which the calibration particles are captured on the capturing unit by eye or by using a microscope or the like when calibrating the irradiation axis of particles that enter the particle composition analysis device relative to the capturing unit.

In one aspect, the present disclosure provides a multifunctional particle analysis device, including: a particle input unit that inputs particles in an aerosol to be measured; a particle measuring device that irradiates the particles input by the particle input unit with laser light and measures a number and a size of the particles in accordance with scattered light produced when the laser light hits the particles; a particle composition analysis device in which the particles input by the particle input unit are captured using a capturing unit and then irradiated with an energy beam to make the captured particles vaporize, sublimate, or react so as to produce desorption components, the desorption components being analyzed in order to analyze a composition and a mass composition of the particles; a particle measuring device calibration unit for calibrating the particle measuring device; and a particle composition analysis device calibration unit for calibrating the particle composition analysis device, wherein when calibration particles for which at least a number, size, and composition thereof are known are input to the particle measuring device and the particle composition analysis device by the particle input unit and then analyzed, the particle measuring device calibration unit calibrates a sensitivity of the particle measuring device in accordance with the number and the size of the calibration particles as measured by the particle measuring device, and wherein the particle composition analysis device calibration unit calibrates a sensitivity of the particle composition analysis device in accordance with a mass composition of the calibration particles as measured by the particle composition analysis device when the calibration particles were analyzed.

The multifunctional particle analysis device in one aspect of the present invention makes it possible to perform a variety of analyses on the particles to be measured using the particle measuring device and the particle composition analysis device. Moreover, the sensitivity of the particle measuring device and the sensitivity of the particle composition analysis device can be calibrated at the same time and using the same calibration particles, thereby making it possible to reduce the effort required to calibrate the device in comparison with using separate calibration procedures.

In one aspect, the present disclosure provides a multifunctional particle analysis device, including: a particle input unit that inputs particles in an aerosol to be measured; a particle measuring device that irradiates the particles input by the particle input unit with laser light and measures a number and a size of the particles in accordance with scattered light produced when the laser light hits the particles; a particle composition analysis device in which the particles input by the particle input unit are captured using a capturing unit and then irradiated with an energy beam to make the captured particles vaporize, sublimate, or react so as to produce desorption components, and then the desorption components are analyzed in order to analyze a composition and a mass composition of the particles; a particle measuring device calibration unit for calibrating the particle measuring device; and a particle composition analysis device calibration unit for calibrating the particle composition analysis device, wherein when calibration particles for which at least a number, size, and composition thereof are known are input to the particle measuring device and the particle composition analysis device by the particle input unit and then analyzed, the particle measuring device calibration unit calibrates a sensitivity of the particle measuring device in accordance with the number and the size of the calibration particles as measured by the particle measuring device, and wherein the particle composition analysis device calibration unit calibrates an irradiation axis of particles that enter the particle composition analysis device relative to the capturing unit in accordance with a state in which the calibration particles were captured on the capturing unit when the calibration particles were analyzed.

The multifunctional particle analysis device in one aspect of the present invention makes it possible to perform a variety of analyses on the particles to be measured using the particle measuring device and the particle composition analysis device. Moreover, the sensitivity of the particle measuring device and the irradiation axis of particles that enter the particle composition analysis device relative to the capturing unit can be calibrated at the same time and using the same calibration particles, thereby making it possible to reduce the effort required to calibrate the device in comparison with using separate calibration procedures.

In the multifunctional particle analysis device in one aspect of the present invention, it is preferable that the particle composition analysis device calibration unit also calibrate an irradiation axis of particles that enter the particle composition analysis device relative to the capturing unit in accordance with a state in which the calibration particles were captured on the capturing unit when the calibration particles were analyzed. This makes it possible to perform a variety of analyses on the particles to be measured using the particle measuring device and the particle composition analysis device. Moreover, the sensitivity of the particle measuring device, the sensitivity of the particle composition analysis device, and the irradiation axis of particles that enter the particle composition analysis device relative to the capturing unit can all be calibrated at the same time and using the same calibration particles, thereby making it possible to reduce the effort required to calibrate the device in comparison with using separate calibration procedures.

In the multifunctional particle analysis device in one aspect of the present invention, it is preferable that the particle composition analysis device include a mass spectrometer. This makes it possible use the mass spectrometer to more easily and accurately analyze the composition and mass composition of the particles.

In the multifunctional particle analysis device in one aspect of the present invention, it is preferable that the particle measuring device include a laser light-emitting unit that irradiates the input particles with laser light, a light-collecting optical system that collects scattered light from the particles at a plurality of positions, photodetectors that convert the light collected by the light-collecting optical system to electrical signals, and a particle diameter distribution calculating unit that calculates a particle diameter distribution for the particles from an intensity of the scattered light detected at the plurality of positions by the photodetectors. This makes it possible to more easily and accurately measure the number and size of the particles using a representative particle size distribution.

The method of calibrating the multifunctional particle analysis device in at least one aspect of the present invention makes it possible to calibrate, at the same time and using the same calibration particles, the particle measuring device and the particle composition analysis device that is integrated into the multifunctional particle analysis device for performing a variety of analyses on the particles to be measured. This makes it possible to reduce the effort required to calibrate the device in comparison with using separate calibration procedures.

The multifunctional particle analysis device in at least one aspect of the present invention includes both a particle measuring device and a particle composition analysis device and therefore makes it possible to perform a variety of analyses on the particles to be measured. Moreover, the particle measuring device and the particle composition analysis device can be calibrated at the same time and using the same calibration particles, thereby making it possible to reduce the effort required to calibrate the device in comparison with using separate calibration procedures.

It is to be understood that both the foregoing general description and the following detailed description are exemplary and explanatory, and are intended to provide further explanation of the invention as claimed.

DETAILED DESCRIPTION OF EMBODIMENTS

Next, various aspects of the present invention will be described in detail with reference to figures.

Figure 1:
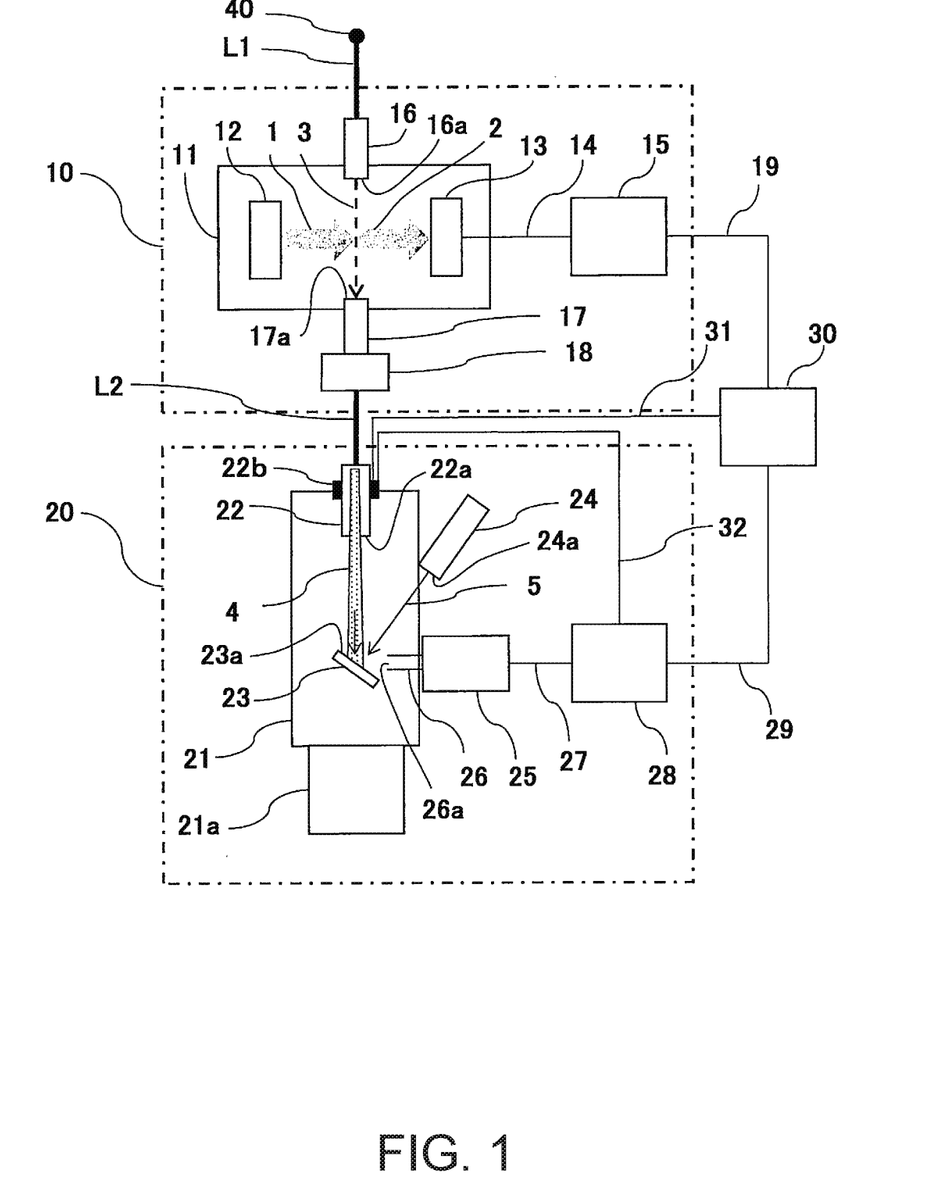
FIG. 1 schematically illustrates a first embodiment of a multifunctional particle analysis device of the present invention.

FIG. 1 schematically illustrates a first embodiment of a multifunctional particle analysis device of the present invention. The multifunctional particle analysis device according to the present embodiment includes a particle measuring device 10 and a particle composition analysis device 20 that are connected in series. Next, the basic configurations and basic operation of the particle measuring device 10 and the particle composition analysis device 20 will be described.

First, the basic configuration and basic operation of the particle measuring device 10 will be described. The particle measuring device 10 includes a light-shielding container 11 that provides a region shielded from external light, a laser-emitting unit 12 that emits laser light 1 across a prescribed distance within the light-shielding container 11, a light-receiving unit 13 that receives the scattered light 2 produced when the laser light 1 emitted by the laser-emitting unit 12 hits particles to be measured, a signal transmission unit 14 that transmits electrical signals output from the light-receiving unit 13 according to the intensity of the received light, and a first signal processing unit 15 that receives the electrical signals transmitted from the signal transmission unit 14 and performs calculations or the like using those signals.

Moreover, a sheath air nozzle 16 is arranged going through one of the sidewalls of the light-shielding container 11. Furthermore, an aerosol sample enters a pipe L1 through a sample inlet 40 and exits through an outlet 16*a* with the entire gas-phase dispersion medium enveloped in sheath air, and the resulting beam-shaped sample air 3 passes through the laser light 1.

In addition, a recovery nozzle 17 for recovering the sample air 3 is arranged going through another one of the sidewalls of the light-shielding container 11. The recovery nozzle 17 has a recovery inlet 17*a*, which is arranged facing the outlet 16*a* of the sheath air nozzle 16 and recovers the sample air 3. The other end of the recovery nozzle 17 is connected via a flow rate adjustment unit 18 to a pipe L2, which leads some or all of the recovered sample air 3 to the particle composition analysis device 20. The flow rate adjustment unit 18 includes a mechanism that can keep the flow rate of the recovered sample aerosol constant. A mass flow controller, a flowmeter with a needle valve, or an orifice may be used for the flow rate adjustment unit 18, for example. The sample air 3 can be transported in one direction across a prescribed distance through the light-shielding container 11 by using a prescribed suction mechanism (not illustrated in the figure) such as a suction pump, for example.

The first signal processing unit 15 of the particle measuring device 10 performs calculations or the like using the electrical signals output according to the intensity of the scattered light 2 received when the laser light 1 hits the particles in the sample air 3, thereby making it possible to calculate the number and size of the particles. Note that in the present invention, the phrase "number and size of the particles" also includes the concept of a particle size distribution. Examples of devices that make this type of basic configuration and basic operation possible include the devices disclosed in Japanese Patent Application Laid-Open Publication No. S61-14543 and Japanese Patent Application Laid-Open Publication No. 2012-189483, for example.

Figure 2:
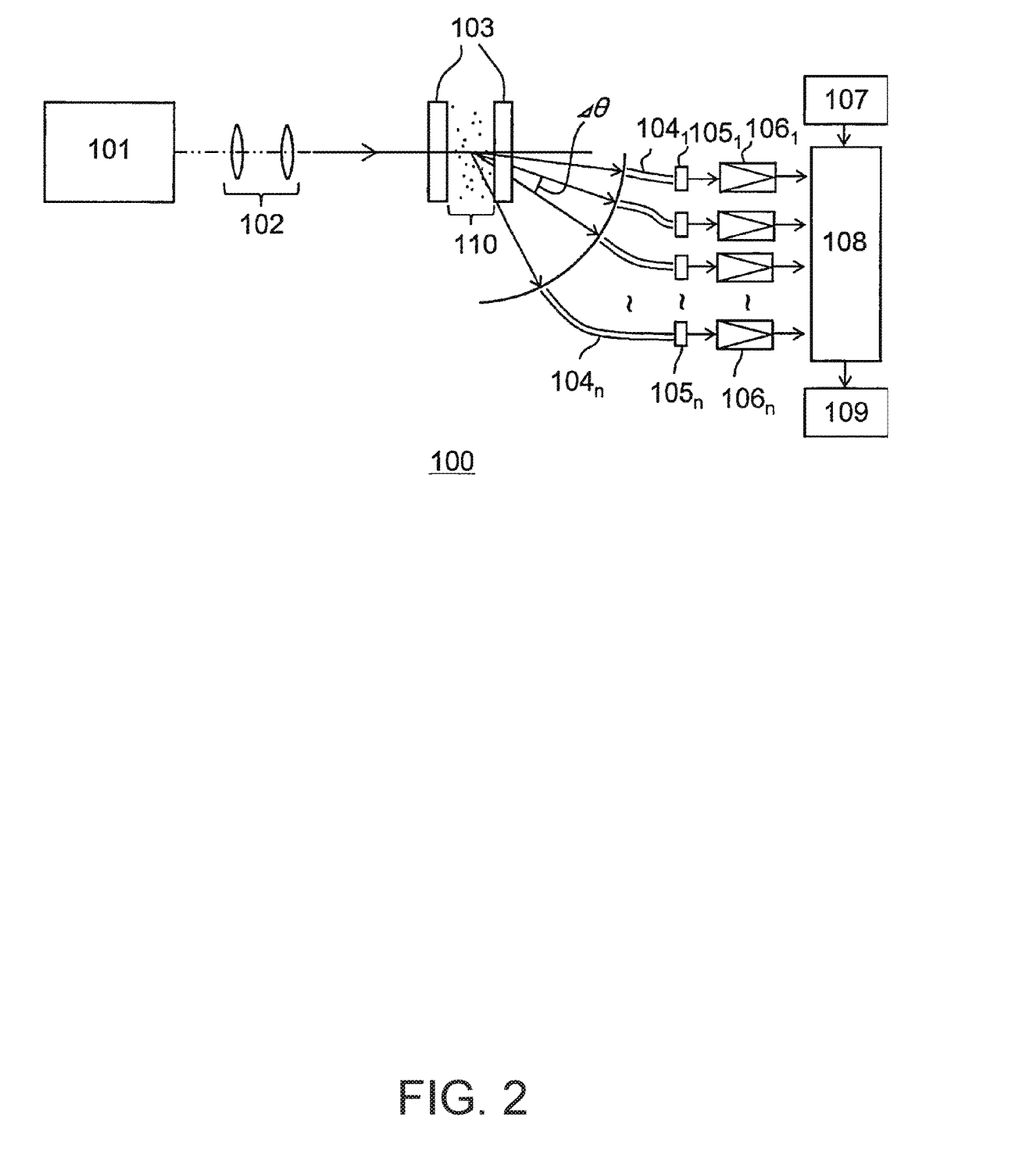
FIG. 2 schematically illustrates the main components of one embodiment of a scattered light detection unit for a particle measuring device that can be integrated into the multifunctional particle analysis device of the present invention.

FIG. 2 schematically illustrates the main components of one embodiment of a scattered light detection unit for a particle measuring device (see Japanese Patent Application Laid-Open Publication No. S61-14543) that can be integrated into at least one aspect of the multifunctional particle analysis device of the present invention.

In this scattered light detection unit 100, laser light generated and output by a laser device 101 (a light-emitting unit) is converted to a parallel laser beam of a prescribed cross-sectional area using a collimator system 102, and this parallel laser beam is then passed through a glass tube 103 to irradiate a group of particles 110 to be measured. Furthermore, the scattered light from the particles is collected by a light-collecting optical system that includes a plurality of light-receiving portions arranged in small intervals $\Delta\theta$ along the scattering angle $\theta$ at equal distances from the position of the group of particles 110. The light collected at each scattering angle $\theta$ is converted to electrical signals by respective photodetectors, and these electrical signals are then input to a computing system 108. In the present embodiment, the ends of the optical fibers $\mathbf{104}_1$ to $\mathbf{104}_n$ are arranged at the light-receiving portions arrayed along the scattering angle $\theta$, and the scattered light travels along the optical fibers $\mathbf{104}_1$ to $\mathbf{104}_n$ and is detected as received light by photodetectors $\mathbf{105}_1$ to $\mathbf{105}_n$. Thus, the optical fibers $\mathbf{104}_1$ to $\mathbf{104}_n$ together constitute a light-collecting optical system that collects scattered light from the particles at a plurality of positions—i.e., at the ends of optical fibers $\mathbf{104}_1$ to $\mathbf{104}_n$, The photodetectors $\mathbf{105}_1$ to $\mathbf{105}_n$ output currents corresponding to the detected light, and these currents are converted to voltages and amplified by amplifiers $\mathbf{106}_1$ to $\mathbf{106}_n$ and then input to the computing system 108.

When a spherical particle of diameter D is irradiated with parallel light of a single color such as laser light, at each angle $\theta$ the intensity of the resulting scattered light $i(D, \theta)$ can be accurately calculated using Mie scattering theory. Moreover, the relationship represented below in equation (1) holds between the scattered light intensity $i(D, \theta)$ from a single particle as obtained on the basis of scattering theory for a group of particles to be measured when irradiated with laser light, the particle size distribution $n_r(D)$, and the scattered light intensity distribution $I(\theta)$.

<#1>

$$I(\theta)=\int i(D,\theta)n_r(D)dD \quad (1)$$

Therefore, the theoretical scattered light intensity distribution $I(\theta)$ obtained when a spherical particle of diameter D is irradiated with parallel light of a single color such as laser light can be calculated.

The scattered light detection unit 100 also includes a conversion table 107. This conversion table 107 stores conversion coefficients obtained by passing a group of reference particles of known particle size and particle size density through the measurement system to irradiate those particles with the laser beam in order to obtain actual measurements of the resulting scattered light intensity distribution, and then calculating the ratios between those measured values and the same theoretical values for each scattering angle. Furthermore, the computing system 108 uses the conversion coefficients obtained by measuring the group of reference particles and stored in the conversion table 107 to implement a calculation process based on the relationship above in order to calculate the number of particles (that is, the number density that corresponds to the number of particles in the group of particles to be measured) and the size of the particles (that is, the absolute particle size distribution) from the intensity of the scattered light detected by the photodetectors. These results are then displayed on a display 109.

Next, the basic configuration and basic operation of the particle composition analysis device 20 will be described. The particle composition analysis device 20 includes a depressurized container 21 that provides a region with reduced pressure relative to the external environment, an exhaust unit 21*a* for maintaining the reduced-pressure state within the depressurized container 21, and an aerodynamic lens 22 that goes through one of the sidewalls of the depressurized container 21 while still maintaining the airtightness thereof. Furthermore, one end of the aerodynamic lens 22 is connected to the pipe L2 that extends from the recovery nozzle 17 of the particle measuring device 10 through the flow rate adjustment unit 18, and some or all of the aerosol sample from the particle measuring device 10 is led to the particle composition analysis device 20. The basic structure of the aerodynamic lens 22 includes a tube-shaped body inside which restrictor mechanisms are arranged. As the aerosol sample passes through this tube-shaped body, the gas-phase components are removed, and the particles converge together into a beam shape and are then emitted as a particle beam.

In the present embodiment, the particle beam 4 is emitted from an outlet 22*a* of the aerodynamic lens 22 and travels through a prescribed distance within the depressurized container 21, and a capturing unit 23 for capturing the particles in the particle beam 4 is arranged at the position where the particles arrive. The basic structure of the capturing unit 23 includes a mesh-shaped portion that has at least a prescribed thickness from a capturing surface 23a side, which is the side that gets irradiated with the particle beam 4. This mesh-shaped structure has a prescribed free area of approximately 80-99%, for example, when projected orthogonally to the direction normal to the capturing unit 23. In addition, the amount of gas-phase components in the particle beam 4 is reduced due to the aerodynamic lens and the reduced-pressure environment inside the depressurized container 21, thereby reducing any disruption due to airflow when the particle beam 4 hits the capturing unit 23. This reduces the kinetic energy of the particles in the particle beam 4 as those particles are captured in the free spaces in the capturing unit 23, thereby making it possible to capture the particles without the particles bouncing off of the capturing unit 23. During this process, it is preferable that the capturing surface 23a of the capturing unit 23 be arranged facing the outlet 22a of the aerodynamic lens 22 at a slight angle relative thereto. This makes it possible to reduce the probability of instances in which particles bounce off of the capturing unit 23 and cannot be captured, thereby making it possible to more efficiently capture the particles in the particle beam 4.

Furthermore, a particle beam emission angle adjustment unit 22b for adjusting the angle of the aerodynamic lens 22 relative to the depressurized container 21 is arranged around the portion of the aerodynamic lens 22 that goes through the depressurized container 21. Specific examples of possible configurations for the particle beam emission angle adjustment unit 22b include structures that make it possible to adjust the angle while maintaining an airtight seal, such as a bellows mechanism, for example. This makes it possible to change the irradiation axis of the particle beam 4 relative to the capturing unit 23, thereby making it possible to correct the position at which the particles that enter the particle composition analysis device 20 are captured by the capturing unit 23 within a desired capturing region.

The particle composition analysis device 20 also includes an energy beam emitter 24 that emits an energy beam 5 such as laser light towards the capturing unit 23, a mass spectrometer 25 that can analyze the components and component masses of a target substance, a signal transmission unit 27 that transmits analysis signals output according to the strength of peaks in the analysis, and a second signal processing unit 28 that receives the analysis signals transmitted from the signal transmission unit 27 and performs calculations or the like using those signals. The energy beam emitter 24 emits the energy beam 5 from an emission opening 24a. This energy beam 5 passes through a transmissive window (not illustrated in the figure) arranged in one of the sidewalls of the depressurized container 21, enters the depressurized container 21, arrives at the capturing unit 23, and irradiates a prescribed region on the capturing unit 23 to make the particles captured thereby vaporize, sublimate, or react so as to produce desorption components. Moreover, the capturing surface 23a of the capturing unit 23 is arranged facing the emission opening 24a of the energy beam emitter 24 at a slight angle relative thereto. This makes the energy beam 5 incident on the capturing surface 23a from a slightly angled direction when viewing from above the capturing surface 23a from a direction orthogonal thereto. This makes it easier for the energy beam 5 to reach the particles captured by the capturing unit 23, thereby making it possible to more efficiently cause the particles captured by the capturing unit 23 to vaporize, sublimate, or react and produce desorption components.

Furthermore, a desorption component collection tube 26 is arranged going through one of the sidewalls of the depressurized container 21 while maintaining the airtightness thereof. The desorption components from the capturing unit 23 are collected through a collection inlet 26a, and the other end of the desorption component collection tube 26 is connected to the mass spectrometer 25. The collected desorption components are fed into the mass spectrometer 25, which then analyzes those components.

The second signal processing unit 28 of the particle composition analysis device 20 performs calculations or the like using the analysis signals output from the mass spectrometer 25 according to the strength of peaks in the analysis, thereby making it possible to calculate the components and component masses of the particles. Examples of particle composition analysis devices with this type of basic configuration and basic operation include the particle composition analysis device disclosed in WO 2011/114587, for example.

In addition to the particle measuring device 10 and the particle composition analysis device 20 described above, the multifunctional particle analysis device in at least one aspect of the present invention also includes a third signal processing unit 30. This third signal processing unit 30 receives measurement signals output from the first signal processing unit 15 of the particle measuring device 10 via a signal transmission unit 19 and performs calculations or the like using those signals, and also simultaneously receives measurement signals output from the second signal processing unit 28 of the particle composition analysis device 20 via a signal transmission unit 29 and performs calculations or the like using those signals. As will be described below, together these signal processing units form a calibration unit that can be used to control the particle measuring device 10 and/or the particle composition analysis device 20 in at least one aspect of the present invention.

More specifically, the third signal processing unit 30 is connected to the first signal processing unit 15 of the particle measuring device 10 via the signal transmission unit 19 and is connected to the second signal processing unit 28 of the particle composition analysis device 20 via the signal transmission unit 29. The third signal processing unit 30 is also connected to the particle beam emission angle adjustment unit 22b via a signal transmission unit 31. Furthermore, the third signal processing unit 30 can perform calculations, control operations, and the like such as the following: receiving measurement signals corresponding to the results of measurements of characteristics of the particles such as the number and size thereof as measured by the particle measuring device 10 and output by the first signal processing unit 15; receiving measurement signals corresponding to the results of measurements of characteristics of the particles such as the components and component masses thereof as measured by the particle composition analysis device 20 and output by the second signal processing unit 28; storing those measurement signals; comparing those measurement signals to pre-stored reference tables; performing determinations based on the results of such comparisons; sending control signals to the light-receiving unit 13 of the particle measuring device 10 via the first signal processing unit 15 and the signal transmission unit 14; sending control signals to the mass spectrometer 25 of the particle composition analysis device 20 via the second signal processing unit 28 and the signal transmission unit 27; and sending control signals to the particle beam emission angle adjustment unit 22b via the signal transmission unit 31 or via the second signal processing unit 28 and a signal transmission unit 32. Moreover, the third signal processing unit 30 and the first signal processing unit 15 may be configured to make it possible to control the flow rate adjustment unit 18 and the laser-emitting unit 12 by sending control signals thereto via additional signal transmission units (not illustrated in the figure). Similarly, the third signal processing unit 30 and the second signal processing unit 28 may be configured to make it possible to control the energy beam emitter 24 by sending control signals thereto via an additional signal transmission unit (not illustrated in the figure).

In the embodiment illustrated in FIG. 1, the first signal processing unit 15, the second signal processing unit 28, and the third signal processing unit 30 are depicted as separate components. However, these components do not necessarily need to be provided separately in order to constitute the calibration unit of the present invention. All three of these components may be integrated together, or any two of these components may be integrated together and the other provided separately. Alternatively, the first signal processing unit 15 may function as a calibration unit for the particle measuring device 10, the second signal processing unit 28 may function as a calibration unit for the particle composition analysis device 20, and the third signal processing unit 28 may be omitted.

Furthermore, in the embodiment illustrated in FIG. 1, the pipe L1 functions as a unit for bringing in the sample for both the particle measuring device 10 and the particle composition analysis device 20. In other words, the pipe L1 functions as a particle input unit that brings in the particles in the aerosol to be measured.

Figure 3:
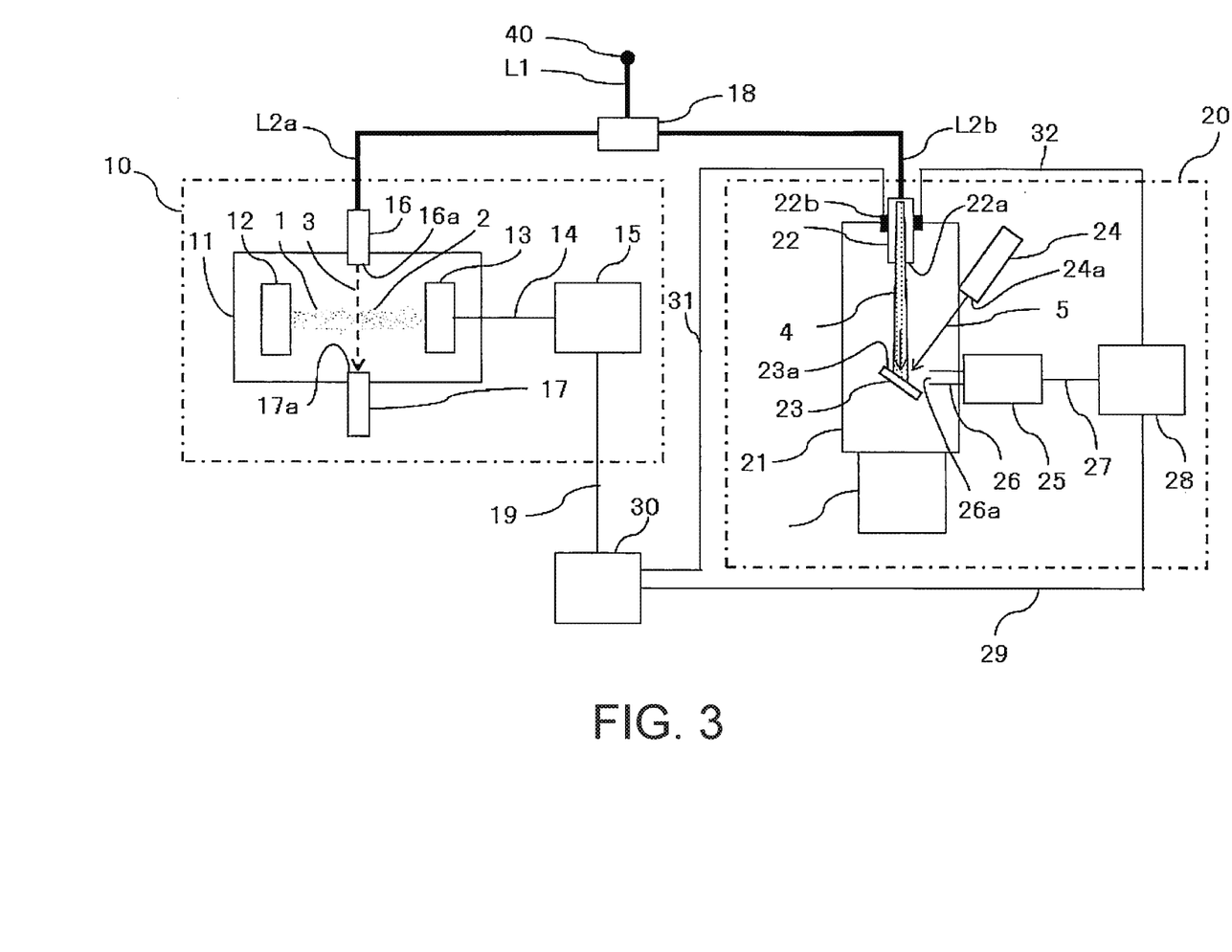
FIG. 3 schematically illustrates a second embodiment of a multifunctional particle analysis device of the present invention.

FIG. 3 schematically illustrates a second embodiment of a multifunctional particle analysis device of the present invention. In the present embodiment, the particle measuring device 10 and the particle composition analysis device 20 of the multifunctional particle analysis device are connected in parallel. In other words, the path for bringing in the aerosol sample from the sample inlet 40 to the device is still constituted by the pipe L1, but the pipe L1 also branches into a pipe L2a and a pipe L2b. The aerosol sample is supplied to the particle measuring device 10 via the pipe L2a and is supplied to the particle composition analysis device 20 via the pipe L2b. In the particle measuring device 10, the aerosol sample is exhausted outside of the system via the recovery nozzle 17 after the measurement is complete. A flow rate adjustment unit 18 that can keep the flow rate of the aerosol sample constant is arranged at the branching portion between the pipe L2a and the pipe L2b. A mass flow controller, a flowmeter with a needle valve, or an orifice may be used for the flow rate adjustment unit 18, for example. The other aspects of the basic configuration and the basic operation of the present embodiment are the same as in the first embodiment illustrated in FIG. 1, and therefore a description of those aspects will be omitted here. Furthermore, in the embodiment illustrated in FIG. 3, the pipe L1 functions as a unit for bringing in the sample for both the particle measuring device 10 and the particle composition analysis device 20. In other words, the pipe L1 functions as a particle input unit that brings in the particles in the aerosol to be measured.

Next, the present invention will be described in further detail with reference to FIGS. 4 to 9.

Figure 4:
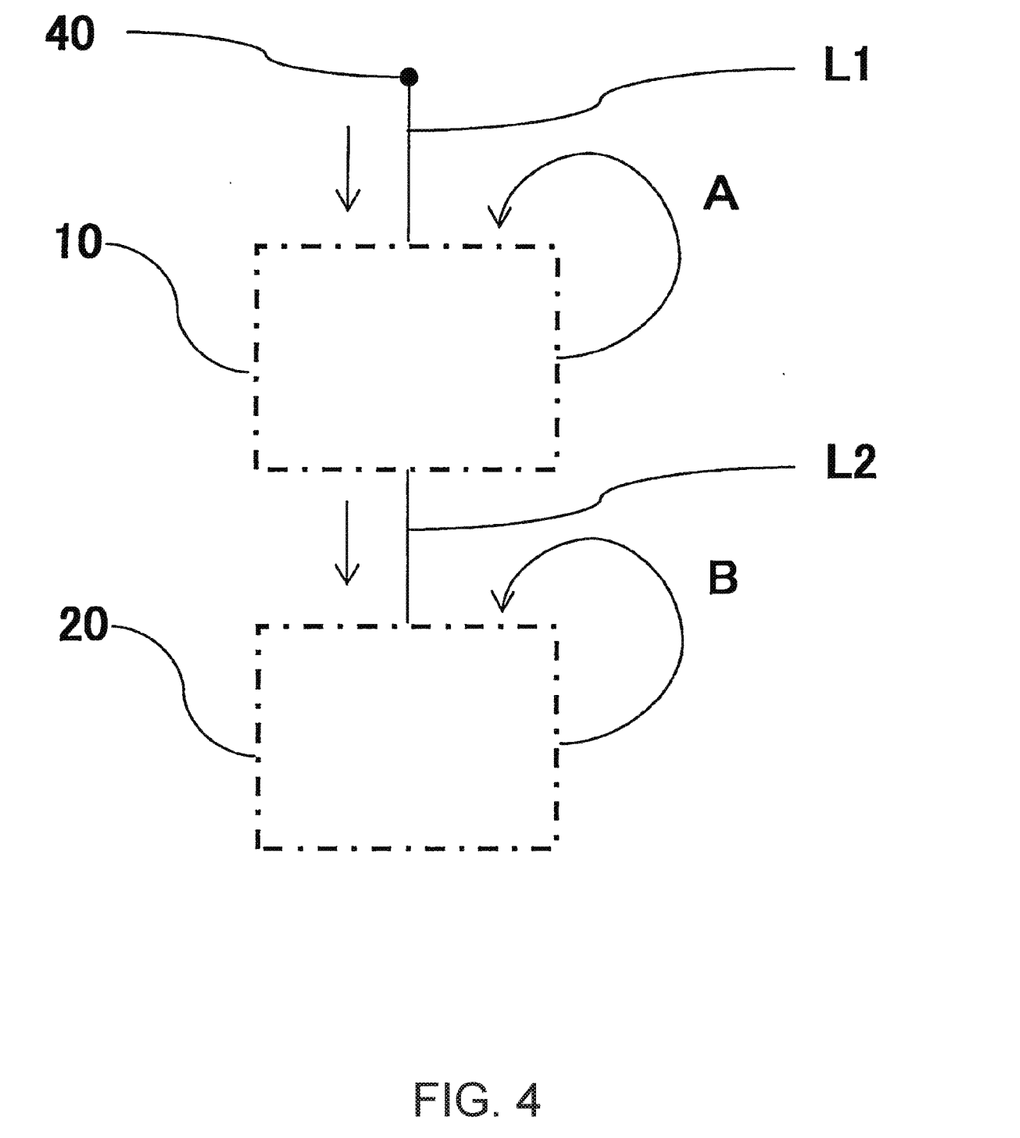
FIG. 4 schematically illustrates a first embodiment of a method of calibrating a multifunctional particle analysis device of the present invention.

FIG. 4 schematically illustrates a first embodiment of a method of calibrating a multifunctional particle analysis device of the present invention. Like the first embodiment of the multifunctional particle analysis device illustrated in FIG. 1, the multifunctional particle analysis device to be calibrated using the method of calibrating of the present embodiment includes a particle measuring device 10 and a particle composition analysis device 20 that are connected in series. Calibration particles for which at least the number, size, and composition are known are input from a sample inlet 40 to the particle measuring device 10 via a pipe L1, and some or all of the calibration particles that pass through the particle measuring device 10 then enter the particle composition analysis device 20 via a pipe L2. Next, a calibration process A is performed to calibrate the sensitivity of the particle measuring device 10 according to the number and size of the calibration particles as measured by the particle measuring device 10, and a calibration process B is performed to calibrate the sensitivity of the particle composition analysis device 20 according to the mass composition of the calibration particles as measured by the particle composition analysis device 20. The calibration particles as well as specific embodiments of the calibration processes A and B will be described later.

Figure 5:
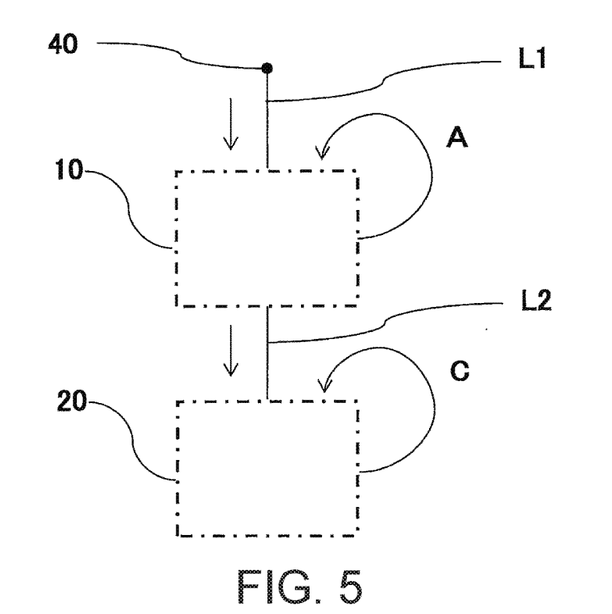
FIG. 5 schematically illustrates a second embodiment of the method of calibrating a multifunctional particle analysis device of the present invention.

FIG. 5 schematically illustrates a second embodiment of a method of calibrating a multifunctional particle analysis device of the present invention. Like the first embodiment of the multifunctional particle analysis device illustrated in FIG. 1, the multifunctional particle analysis device to be calibrated using the method of calibrating of the present embodiment includes a particle measuring device 10 and a particle composition analysis device 20 that are connected in series. Calibration particles for which at least the number, size, and composition are known are input from a sample inlet 40 to the particle measuring device 10 via a pipe L1, and some or all of the calibration particles that pass through the particle measuring device 10 then enter the particle composition analysis device 20 via a pipe L2. Next, a calibration process A is performed to calibrate the sensitivity of the particle measuring device 10 according to the number and size of the calibration particles as measured by the particle measuring device 10, and a calibration process C is performed to calibrate the position at which particles that enter the particle composition analysis device 20 are captured by a capturing unit according to the state in which the calibration particles are captured on the capturing unit of the particle composition analysis device 20. The calibration particles as well as specific embodiments of the calibration processes A and C will be described later.

Figure 6:
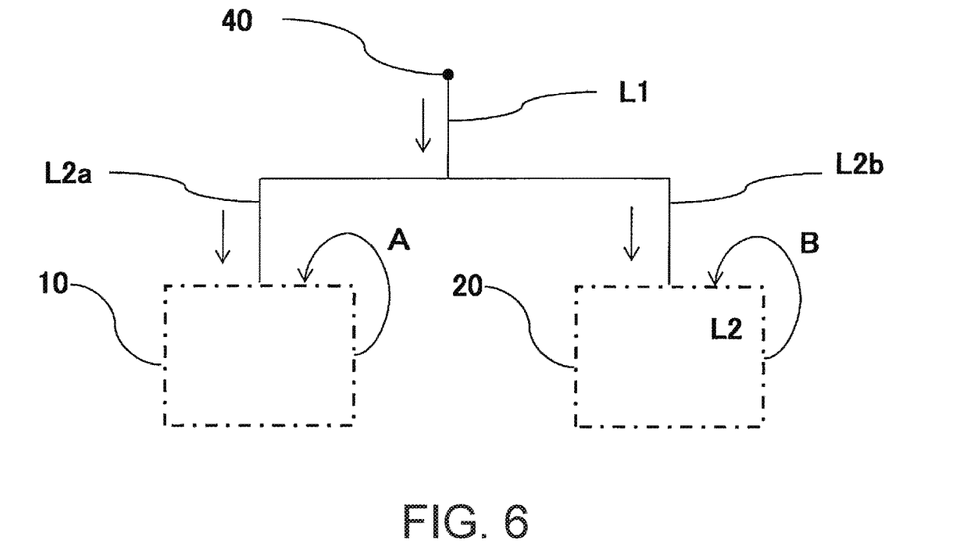
FIG. 6 schematically illustrates a third embodiment of a method of calibrating a multifunctional particle analysis device of the present invention.

FIG. 6 schematically illustrates a third embodiment of a method of calibrating a multifunctional particle analysis device of the present invention. Like the second embodiment of the multifunctional particle analysis device illustrated in FIG. 3, the multifunctional particle analysis device to be calibrated using the method of calibrating of the present embodiment includes a particle measuring device 10 and a particle composition analysis device 20 that are connected in parallel. Calibration particles for which at least the number, size, and composition are known are input from a sample inlet 40 to a pipe L1. Some of the calibration particles are led to the particle measuring device 10 via a pipe L2a that branches off the pipe L1, and the rest of the calibration particles are led to the particle composition analysis device 20 via a pipe L2b that also branches off the pipe L1. Next, a calibration process A is performed to calibrate the sensitivity of the particle measuring device 10 according to the number and size of the calibration particles as measured by the particle measuring device 10, and a calibration process B is performed to calibrate the sensitivity of the particle composition analysis device 20 according to the mass composition of the calibration particles as measured by the particle composition analysis device 20. The calibration particles as well as specific embodiments of the calibration processes A and B will be described later.

Figure 7:
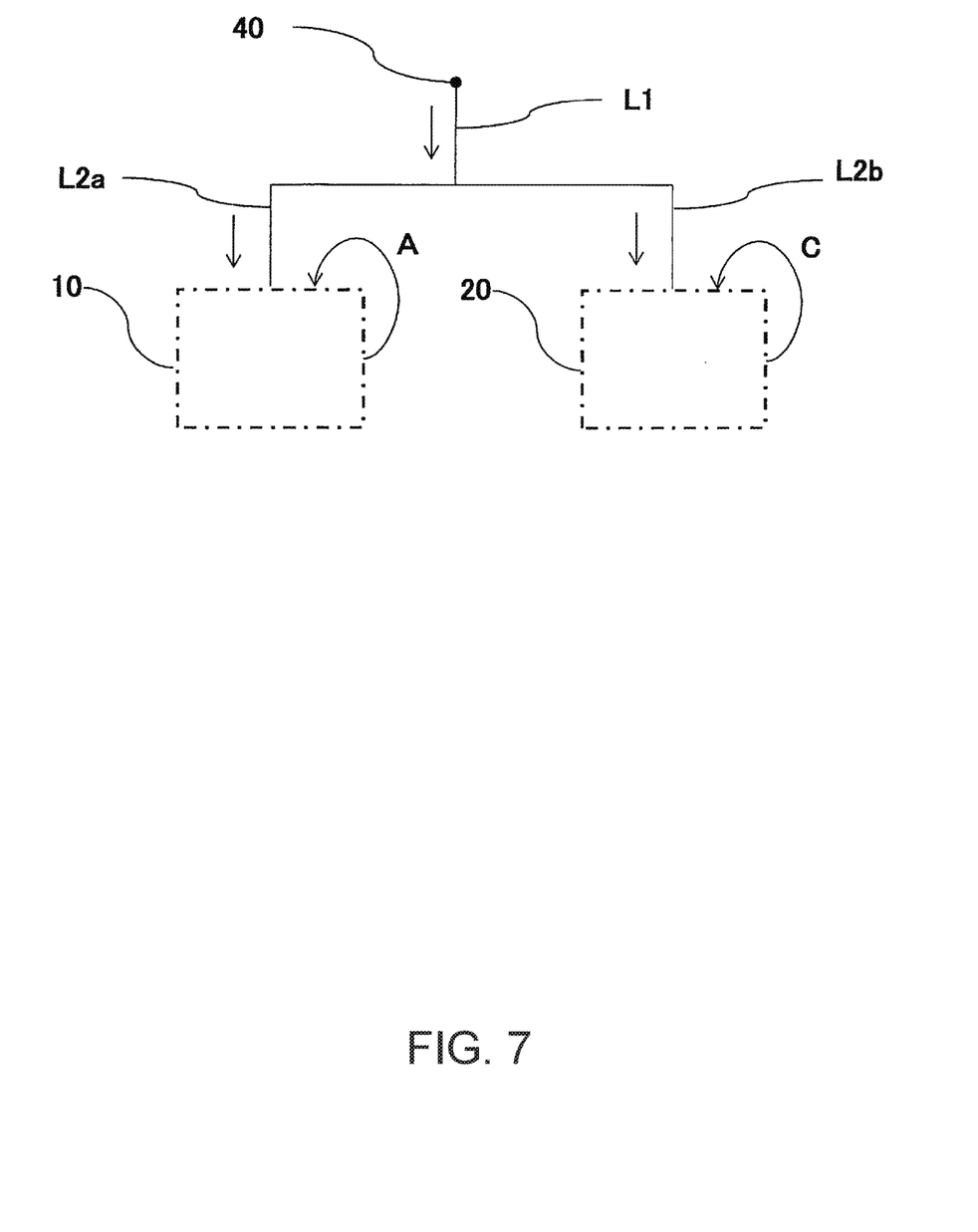
FIG. 7 schematically illustrates a fourth embodiment of a method of calibrating a multifunctional particle analysis device of the present invention.

FIG. 7 schematically illustrates a fourth embodiment of a method of calibrating a multifunctional particle analysis device of the present invention. Like the second embodiment of the multifunctional particle analysis device illustrated in FIG. 3, the multifunctional particle analysis device to be calibrated using the method of calibrating of the present embodiment includes a particle measuring device 10 and a particle composition analysis device 20 that are connected in parallel. Calibration particles for which at least the number, size, and composition are known are input from a sample inlet 40 to a pipe L1. Some of the calibration particles are led to the particle measuring device 10 via a pipe L2a that branches off the pipe L1, and the rest of the calibration particles are led to the particle composition analysis device 20 via a pipe L2b that also branches off the pipe L1. Next, a calibration process A is performed to calibrate the sensitivity of the particle measuring device 10 according to the number and size of the calibration particles as measured by the particle measuring device 10, and a calibration process C is performed to calibrate the position at which particles that enter the particle composition analysis device 20 are captured by a capturing unit according to the state in which the calibration particles are captured on the capturing unit of the particle composition analysis device 20. The calibration particles as well as specific embodiments of the calibration processes A and C will be described later.

Note that in the embodiments illustrated in FIGS. 4 to 7, the calibration processes B and C for the particle composition analysis device 20 are depicted as being performed separately. However, these calibration processes may also be integrated together. This makes it possible to perform the calibration process A for calibrating the sensitivity of the particle measuring device 10 as well as the calibration process B for calibrating the sensitivity of the particle composition analysis device 20 and the calibration process C for calibrating the irradiation axis of the particles that enter the particle composition analysis device 20 relative to the capturing unit all at the same time and using the same calibration particles, thereby making it possible to reduce the effort associated with calibrating the device even further.

<Calibration Particles>

The types of particles used for the calibration particles are not particularly limited, and any particles may be used as long as those particles can serve as a standard for particle number and particle size measurements by the particle measuring device 10 and can also serve as a standard for particle component and component mass analyses with the particle composition analysis device 20. However, it is preferable that organic polymer particles such as polystyrene latex particles be used. Organic polymer particles such as polystyrene latex particles can be prepared as a monodispersion that exhibits an extremely narrow particle size distribution in comparison with polydisperse particles made of an inorganic compound. This makes it possible to establish an accurate correlation between the number and size of calibration particles input to the device and the strength of the resulting detection signals from the device, thereby making it possible to more precisely calibrate the sensitivity of the particle measuring device 10. This also makes it possible to accurately calculate the masses of the calibration particles from the number, size, and composition thereof, which in turn makes it possible to establish an accurate correlation between the input mass and the strength of the resulting detection signals from the device, thereby making it possible to more precisely calibrate the sensitivity of the particle composition analysis device 20.

In a preferred embodiment of the present invention, it is preferable that the calibration particles be visibly marked. This makes it possible to easily verify the state in which the calibration particles are captured on a capturing unit 23 when input to the particle composition analysis device 20 by eye or by using a fluorescence microscope or the like, thereby making it possible to more easily adjust the position at which the particles that enter the device are captured by the capturing unit 23. Fluorescent polystyrene latex particles (made by JST) or the like are commercially available and can be used preferably, for example.

<Calibration Process A>

The calibration process A is used to calibrate the sensitivity of the particle measuring device 10. More specifically, an aerosol sample that contains the calibration particles (below, referred to simply as a "calibration aerosol sample") is prepared by mixing calibration particles for which at least the number of particles and size and composition thereof are known together with clean air in a prescribed ratio. Then, as shown in step S1 in the flowchart in FIG. 8 and in step S10 in the flowchart in FIG. 9, the number of calibration particles that will be input to the particle measuring device 10 is calculated in advance from the volume of the calibration aerosol sample that will be input to the device. Note that the volume of the calibration aerosol sample input to the particle measuring device 10 can also be set and adjusted using the flow rate adjustment unit 18 of the embodiments illustrated in FIGS. 1 and 3. Then, as shown in steps S2 and S11 in FIGS. 8 and 9, the calibration aerosol sample is input to the particle measuring device 10, and as shown in steps S3 and S12 in FIGS. 8 and 9, the number and size of the particles is calculated by a first signal processing unit 15 of the particle measuring device 10. Next, as shown in steps S4 and S13 in FIGS. 8 and 9, these calculated values are compared to the known values for the calibration particles, and as shown in steps S5 and S14 in FIGS. 8 and 9, the sensitivity of the particle measuring device 10 is calibrated such that these calculated values become equal to the known values for the calibration particles. Here, "calibrating the sensitivity" refers to changing the values of calibration coefficients stored in the first signal processing unit 15 and a third signal processing unit 30, changing the flow rate of a flow rate adjustment unit 18, or changing the output of a laser-emitting unit 12, for example, in order to maintain the precision of the device. Moreover, the phrase "become equal" also includes cases in which the values calculated by the device are adjusted to be closer to the known values of the calibration particles in order to maintain the precision of the device.

<Calibration Process B>

The calibration process B is used to calibrate the sensitivity of the particle composition analysis device 20. More specifically, similar to the calibration process A and as shown in step S1 in the flowchart in FIG. 8, the mass of the calibration particles that will be input to the particle composition analysis device 20 is calculated in advance from the volume of the calibration aerosol sample that will be input to the device. Note that the volume of the calibration aerosol sample input to the particle composition analysis device 20 can also be adjusted using the flow rate adjustment unit 18 of the embodiments illustrated in FIGS. 1 and 3. Then, as shown in step S6 in FIG. 8, the calibration aerosol sample is input to the particle composition analysis device 20, and as shown in step S7 in FIG. 8, the components and component masses of the particles are calculated by a second signal processing unit 28 of the particle composition analysis device 20. Next, as shown in step S8 in FIG. 8, these calculated values are compared to the known values for the calibration particles, and as shown in step S9 in FIG. 8, the sensitivity of the particle composition analysis device 20 is calibrated such that these calculated values become equal to the known values for the calibration particles. Here, "calibrating the sensitivity" refers to changing the values of calibration coefficients stored in the second signal processing unit 28 and the third signal processing unit 30, changing the multiplication factor of a mass spectrometer 25, or changing the output of an energy beam emitter 24, for example, in order to maintain the precision of the device. Moreover, the phrase "become equal" also includes cases in which the values calculated by the device are adjusted to be closer to the known values of the calibration particles in order to maintain the precision of the device.

<Calibration Process C>

Figure 9:
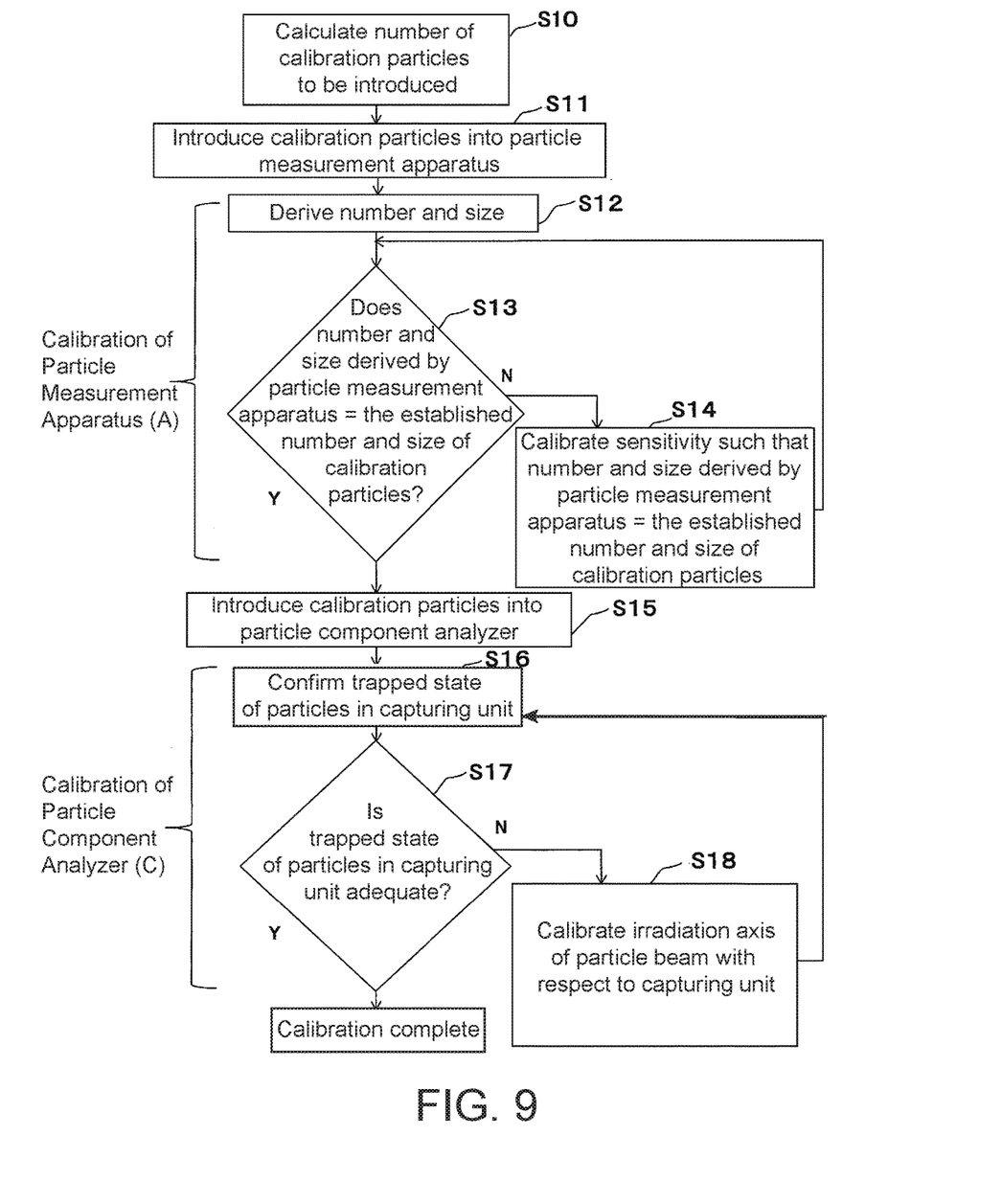
FIG. 9 is a flowchart illustrating another embodiment of controlling a multifunctional particle analysis device using the method of calibrating of the present invention.

In the calibration process C, as shown in step S15 of the flowchart in FIG. 9, the calibration aerosol sample is input to the particle composition analysis device 20, and as shown in step S16 in FIG. 9, the state in which the calibration particles are captured on the capturing unit 23 is verified. Furthermore, as shown in step S17 of FIG. 9, it is determined whether the capturing state of the particles on the capturing unit is acceptable, and if the capturing state is determined to not be acceptable, the irradiation axis of a particle beam 4 relative to the capturing unit 23 is calibrated, as shown in step S18 in FIG. 9.

As a method for verifying the capturing state of the calibration particles and determining whether that state is acceptable, the position at which the calibration particles are captured on the capturing unit 23 may be verified directly, or if the strength of the detection signal from the particle composition analysis device 20 for the calibration particles is weaker than a pre-defined range, this data may be used as an indicator that the capturing state of the calibration particles on the capturing unit 23 is not acceptable. Examples of methods for directly verifying the position at which the calibration particles are captured on the capturing unit 23 include methods such as: (1) inputting fluorescently marked calibration particles into the device, capturing the calibration particles on a filter such as a quartz filter that is arranged in advance at the same position where the capturing unit 23 will be arranged, recovering the filter, irradiating the filter with excitation light to make the captured calibration particles emit fluorescent light and then observing the resulting fluorescent light by eye or using a microscope or the like, and observing the position at which the calibration particles are captured (2) leaving the filter in the device and precisely irradiating the filter with an excitation energy beam from the energy beam emitter 24 in the same prescribed region in which particles should be captured on the capturing unit 23, and observing the resulting fluorescent light from the captured and fluorescently marked particles. Furthermore, whether the position at which the particles are captured on the capturing unit 23 is acceptable can be determined as follows, for example. A prescribed capturing region in which the particles should be captured on the capturing unit 23 is defined in advance, and a filter is arranged at that prescribed capturing region. The position at which the calibration particles are captured on the filter is then projected out onto a plane orthogonal to the normal direction of a capturing surface 23a that gets irradiated with the particle beam 4. If the center of the projected position at which the particles are captured, a prescribed area of that position, or the like is within a prescribed radius of the prescribed capturing region, or if that prescribed area occupies greater than or equal to a prescribed amount of the prescribed capturing region, or the like, it can be determined that the state in which the particles are captured on the capturing unit 23 is acceptable.

Meanwhile, if the state in which the particles are captured on the capturing unit is not acceptable, the irradiation axis of the particle beam 4 relative to the capturing unit 23 is calibrated to correct the capturing state. Examples of methods for doing this include methods such as arranging a particle beam emission angle adjustment unit 22b around the portion of an aerodynamic lens 22 that goes through a depressurized container 21, and then adjusting the angle of the aerodynamic lens 22 relative to the depressurized container 21 in order to change the irradiation axis of the particle beam 4 relative to the capturing unit 23, for example.

Moreover, even if the individual calibration particles used in calibration process A to calibration process C are not perfectly uniform or homogeneous, as long as groups of such non-uniform or non-homogeneous particles exhibit suitable attributes as calibration particles, those particles may of course be used in each of the calibration processes.

Figure 8:
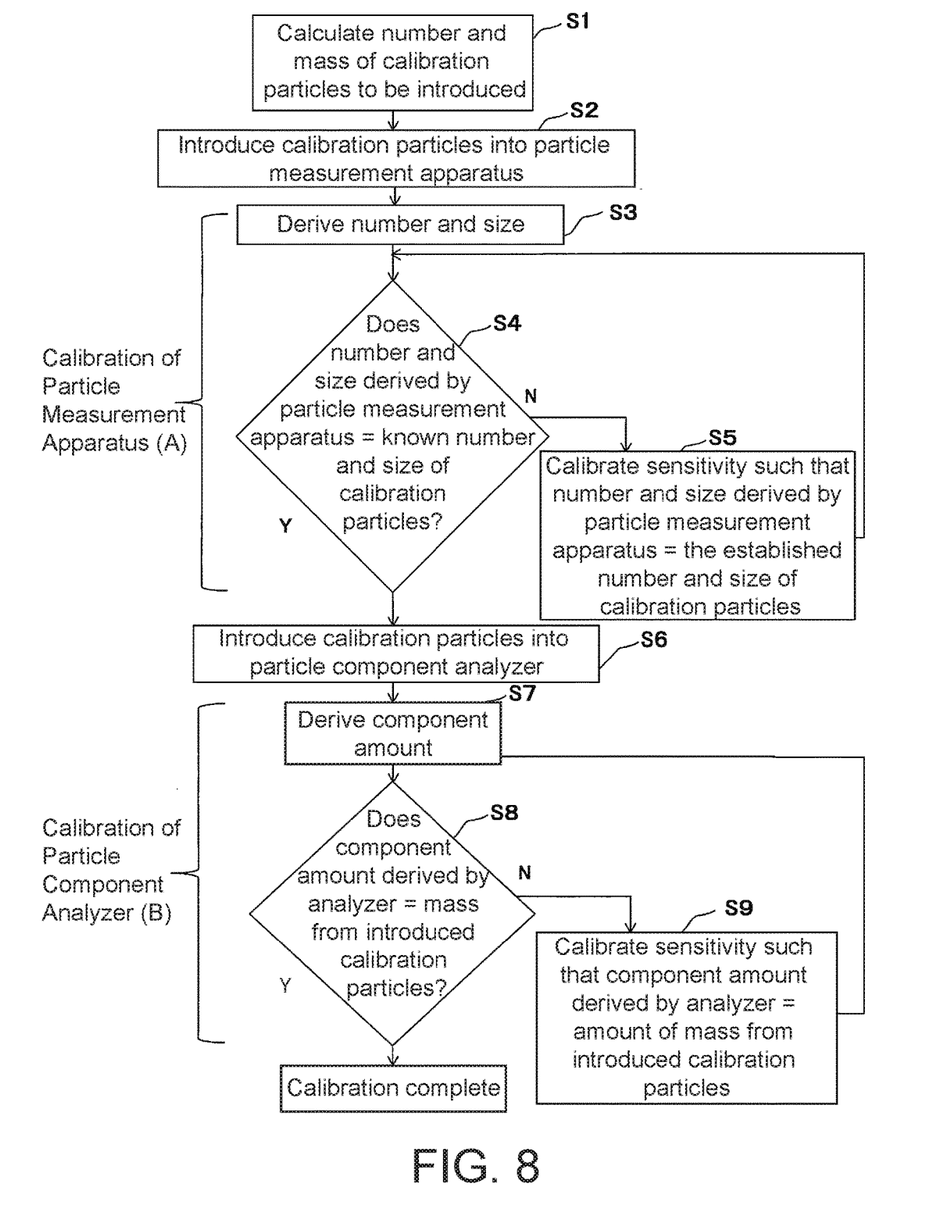
FIG. 8 is a flowchart illustrating one embodiment of controlling a multifunctional particle analysis device using the method of calibrating of the present invention.

FIG. 8 is a flowchart illustrating one embodiment of controlling a multifunctional particle analysis device using the method of calibrating of the present invention. In the present embodiment, a particle measuring device 10 is controlled using a calibration process A and a particle composition analysis device 20 is controlled using a calibration process B in order to maintain the precision of the multifunctional particle analysis device.

Moreover, FIG. 9 is a flowchart illustrating another embodiment of controlling a multifunctional particle analysis device using the method of calibrating of the present invention. In the present embodiment, a particle measuring device 10 is controlled using a calibration process A and a particle composition analysis device 20 is controlled using a calibration process C in order to maintain the precision of the multifunctional particle analysis device.

By implementing control processes such as those illustrated in FIGS. 8 and 9, when the outputs of the particle measuring device 10 and the particle composition analysis device 20 for a pre-defined input amount of calibration particles deviates from the initial values, the device can be controlled to enter a calibration mode in which those deviations are corrected automatically.

Embodiments of the present invention were described above; however, the scope of the present invention is not limited to these embodiments. Moreover, aspects of the configurations of each embodiment described above may be multifunctional as appropriate, and yet other additional configurations are not particularly limited as long as the effects of the present invention are still achieved.

It will be apparent to those skilled in the art that various modifications and variations can be made in the present invention without departing from the spirit or scope of the invention. Thus, it is intended that the present invention cover modifications and variations that come within the scope of the appended claims and their equivalents. In particular, it is explicitly contemplated that any part or whole of any two or more of the embodiments and their modifications described above can be combined and regarded within the scope of the present invention.

What is claimed is:

1. A method of calibrating a multifunctional particle analysis device including a particle measuring device that irradiates particles in an aerosol to be measured with laser light and measures a number and a size of the particles in accordance with scattered light produced when the laser light hits the particles, and a particle composition analysis device in which the particles in the aerosol to be measured are captured using a capturing unit and then irradiated with an energy beam to make the captured particles vaporize, sublimate, or react so as to produce desorption components, the desorption components being analyzed in order to analyze a composition and a mass composition of the particles, the method of calibrating comprising:

preparing a plurality of calibration particles of same kind for which at least a number, size, and composition thereof are known;

dividing the plurality of calibration particles into two groups of first and second groups;

inputting the first group of calibration particles into the particle measuring device and then analyzing the first group of calibration particles by the particle measuring device;

at the same time as inputting the first group of calibration particles into the particle measuring device, inputting the second group of calibration particles into the particle composition analysis device and then analyzing the second group of calibration particles in the particle composition analysis device;

calibrating a sensitivity of the particle measuring device in accordance with the number and the size of the first group of calibration particles as measured by the particle measuring device; and calibrating the particle composition analysis device in accordance with a property of the second group of calibration particles in the particle composition analysis device.

2. The method of calibrating the multifunctional particle analysis device according to claim 1, wherein the calibration of the particle composition analysis device includes calibrating an emission axis of particles that enter the particle composition analysis device relative to the capturing unit in accordance with a state in which the second group of calibration particles are captured on the capturing unit.

3. The method of calibrating the multifunctional particle analysis device according to claim 1, wherein the calibration particles are visibly marked.

4. The method of calibrating the multifunctional particle analysis device according to claim 1, wherein the calibration particles are polystyrene latex particles.

5. The method of calibrating the multifunctional particle analysis device according to claim 1, wherein the calibration of the particle composition analysis device includes calibrating ft sensitivity of the particle composition analysis device in accordance with a mass composition of the second group of calibration particles as measured by the particle composition analysis device.

6. A method of calibrating a multifunctional particle analysis device including a particle measuring device that irradiates particles in an aerosol to be measured with laser light and measures a number and a size of the particles in accordance with scattered light produced when the laser light hits the particles, and a particle composition analysis device in which the particles in the aerosol to be measured are captured using a capturing unit and then irradiated with an energy beam to make the captured particles vaporize, sublimate, or react so as to produce desorption components, the desorption components being analyzed in order to analyze a composition and a mass composition of the particles, the method of calibrating comprising:

preparing a plurality of calibration particles of same kind for which at least a number, size, and composition thereof are known;

inputting the plurality of calibration particles into the particle measuring device and then analyzing the plurality of the calibration particles by the particle measuring device;

calibrating the particle measuring device in accordance with the number and the size of the plurality of calibration particles as measured by the particle measuring device;

transferring the plurality of the plurality of calibration particles that have been analyzed by the particle measuring device to the particle composition analysis device;

calibrating the particle composition analysis device in accordance with a property of the transferred plurality of calibration particles in the particle composition analysis device.

7. The method of calibrating the multifunctional particle analysis device according to claim 6, wherein the calibration particles are polystyrene latex particles.

8. The method of calibrating the multifunctional particle analysis device according to claim 6, wherein the calibration of the particle composition analysis device includes calibrating an emission axis of particles that enter the particle composition analysis device relative to the capturing unit in accordance with a state in which the transferred plurality of calibration particles are captured on the capturing unit.

9. The method of calibrating the multifunctional particle analysis device according to claim 6, wherein the calibration of the particle composition analysis device includes calibrating a sensitivity of the particle composition analysis device in accordance with a mass composition of the transferred plurality of calibration particles as measured by the particle composition analysis device.

10. The method of calibrating the multifunctional particle analysis device according to claim 6, wherein the calibration particles are visibly marked.

11. A multifunctional particle analysis device, comprising:

a particle input unit that inputs particles in an aerosol to be measured, the particle input unit having first and second pipes to which the inputted particles are to be distributed;

a particle measuring device connected to the first pipe, that irradiates particles inputted through the first pipe of the particle input unit with laser light and measures a number and a size of the particles in accordance with scattered light produced when the laser light hits the particles;

a particle composition analysis device connected to the second pipe, that includes an energy beam emitter in which particles inputted through the second pipe of the particle input unit are captured using a capturing unit and then irradiated with an energy beam emitted by the energy beam emitter to make the captured particles vaporize, sublimate, or react so as to produce desorption components, the desorption components being analyzed in order to analyze a composition and a mass composition of the particles;

a particle measuring device calibration unit for calibrating the particle measuring device; and a particle composition analysis device calibration unit for calibrating the particle composition analysis device, wherein the particle input unit receives a plurality of calibration particles of same kind for which at least a number, size, and composition thereof are known, and divides the plurality of calibration particles into two groups of first and second groups that are distributed to the first pipe and the second pipe, respectively, so that the respective first and second groups of calibration particles are analyzed by the particle measuring device and the particle composition analysis device, respectively, wherein the particle measuring device calibration unit calibrates a sensitivity of the particle measuring device in accordance with the number and the size of the first group of calibration particles as measured by the particle measuring device, and wherein the particle composition analysis device calibration unit calibrates the particle composition analysis device in accordance with a property of the second group of calibration particles in the particle composition analysis device.

12. The multifunctional particle analysis device according to claim 11, wherein the particle composition analysis device calibration unit calibrates an emission axis of particles that enter the particle composition analysis device relative to the capturing unit in accordance with a state in which the second group of calibration particles were captured on the capturing unit.

13. The multifunctional particle analysis device according to claim 11, wherein the particle composition analysis device includes a mass spectrometer.

14. The multifunctional particle analysis device according to claim 11, wherein the particle measuring device includes a laser light-emitting unit that irradiates the input particles with laser light, a light-collecting optical system that collects scattered light from the particles at a plurality of positions, photodetectors that convert the light collected by the light-collecting optical system to electrical signals, and a particle diameter distribution calculating unit that calculates a particle diameter distribution for the particles from an intensity of the scattered light detected at the plurality of positions by the photodetectors.

15. The multifunctional particle analysis device according to claim 11, wherein the calibration particles are polystyrene latex particles.

16. The method of calibrating the multifunctional particle analysis device according to claim 11,
wherein the particle composition analysis device calibration unit calibrates a sensitivity of the particle composition analysis device in accordance with a mass composition of the second group of calibration particles as measured by the particle composition analysis device.

17. A multifunctional particle analysis device, comprising:
a particle input unit that inputs particles in an aerosol to be measured;
a particle measuring device connected to the particle input unit, that irradiates the particles inputted by the particle input unit with laser light and measures a number and a size of the particles in accordance with scattered light produced when the laser light hits the particles;
a connection pipe, one end of which is connected to the particle measuring device to receive the particles that have been analyzed by the particle measuring device;
a particle composition analysis device connected to another end of the connection pipe to receive the particles that have been analyzed by the particle measuring device, the particle composition analysis device including an energy beam emitter in which the particles inputted through the connection pipe are captured using a capturing unit and then irradiated with an energy beam emitted by the energy beam emitter to make the captured particles vaporize, sublimate, or react so as to produce desorption components, and then the desorption components are analyzed in order to analyze a composition and a mass composition of the particles;
a particle measuring device calibration unit for calibrating the particle measuring device; and
a particle composition analysis device calibration unit for calibrating the particle composition analysis device,
wherein the particle input unit receives a plurality of calibration particles for which at least a number, size, and composition thereof are known and inputs the plurality of calibration particles to the particle measuring device so that the plurality of calibration particles are analyzed by the particle measuring device,
wherein the particle measuring device calibration unit calibrates a sensitivity of the particle measuring device in accordance with the number and the size of the plurality of calibration particles as measured by the particle measuring device,
wherein the connection pipe transfers the plurality of calibration particles that have been analyzed by the particle measuring device to the particle composition analysis device, and
wherein the particle composition analysis device calibration unit calibrates the particle composition analysis device in accordance with a property of the transferred plurality of calibration particles in the particle composition analysis device.

18. The multifunctional particle analysis device according to claim 17, wherein the calibration particles are polystyrene latex particles.

19. The method of calibrating the multifunctional particle analysis device according to claim 17,
wherein the particle composition analysis device calibration unit calibrates an emission axis of particles that enter the particle composition analysis device relative to the capturing unit in accordance with a state in which the transferred plurality of calibration particles are captured on the capturing unit.

20. The method of calibrating the multifunctional particle analysis device according to claim 17,
wherein the particle composition analysis device calibration unit calibrates a sensitivity of the particle composition analysis device in accordance with a mass composition of the transferred plurality of calibration particles as measured by the particle composition analysis device.

* * * * *